(12) United States Patent
Doo

(10) Patent No.: US 10,383,716 B2
(45) Date of Patent: Aug. 20, 2019

(54) SLING FOR URINARY INCONTINENCE SURGERY

(71) Applicant: Jae Kyun Doo, Jeonju-si (KR)

(72) Inventor: Jae Kyun Doo, Jeonju-si (KR)

( * ) Notice: Subject to any disclaimer, the term of this patent is extended or adjusted under 35 U.S.C. 154(b) by 258 days.

(21) Appl. No.: 15/542,504

(22) PCT Filed: Mar. 7, 2016

(86) PCT No.: PCT/KR2016/002239
§ 371 (c)(1),
(2) Date: Jul. 10, 2017

(87) PCT Pub. No.: WO2016/144065
PCT Pub. Date: Sep. 15, 2016

(65) Prior Publication Data
US 2018/0263750 A1    Sep. 20, 2018

(30) Foreign Application Priority Data

Mar. 6, 2015   (KR) .................. 10-2015-0031319

(51) Int. Cl.
*A61F 2/02*     (2006.01)
*A61F 2/00*     (2006.01)

(52) U.S. Cl.
CPC .... *A61F 2/0045* (2013.01); *A61F 2210/0004* (2013.01); *A61F 2220/005* (2013.01); *A61F 2220/0016* (2013.01); *A61F 2220/0075* (2013.01); *A61F 2250/0007* (2013.01); *A61F 2250/0012* (2013.01); *A61F 2250/0031* (2013.01)

(58) Field of Classification Search
CPC .................................. A61F 2/02; A61F 2/0045
USPC ....................................................... 600/29–32
See application file for complete search history.

(56) References Cited

U.S. PATENT DOCUMENTS

2010/0076254 A1    3/2010   Jimenez et al.
2011/0245589 A1   10/2011   Palma et al.

FOREIGN PATENT DOCUMENTS

KR        20-0332533 Y1    11/2003
KR        10-0824014 B1     4/2008
KR     10-2009-0030418 A    3/2009

*Primary Examiner* — John P Lacyk
(74) *Attorney, Agent, or Firm* — Novick, Kim & Lee, PLLC; Jae Youn Kim

(57) ABSTRACT

Provided is a sling for urinary incontinence surgery. The sling has a mesh tape to be easily mounted by means of a spacing unit disposed in a center part of the mesh tape and also enables optimal tension adjustment of the mesh tape, thereby maximizing the effect of female urinary incontinence treatment surgery. Moreover, the sling can prevent the mesh tape from pressing the urethra excessively, thereby allowing a patient to easily urinate after surgery, and tension adjustment of the mesh tape is very easy.

40 Claims, 7 Drawing Sheets

SLING FOR URINARY INCONTINENCE SURGERY

TECHNICAL FIELD

The present invention relates to a sling for urinary incontinence surgery which prevents a mesh tape from being mounted excessively loosely during conventional female urinary incontinence treatment surgery and thus causing no effect on urinary incontinence treatment surgery and prevents the mesh tape from being excessively deeply and firmly adhered to the urethra and thus causing difficulty in urinating after urinary incontinence treatment surgery.

The mesh tape is easily mounted by means of a spacing unit disposed at the central part of the mesh tape and also enables optimal tension adjustment of the mesh tape so as to maximize the effect of female urinary incontinence treatment surgery.

More particularly, the sling for urinary incontinence surgery prevents the mesh tape from pressing the urethra excessively strongly so as to allow a patient to easily urinate after surgery, and does not have to pull both sides of the mesh tape in the outward direction of lower abdominal tissues of the patient, if the mesh tape is excessively deeply fixed to the inside of the lower abdominal tissues of the patient, and thus facilitates tension adjustment of the mesh tape.

BACKGROUND ART

In general, treatment instruments for urinary incontinence are instruments which treat urinary incontinence, which can occur due to giving birth or menopause.

Urinary incontinence refers to involuntary urine leakage which influences women and the elderly.

That is to say, urinary incontinence means leakage of urine from the bladder to the outside through the urethra regardless of person's will, i.e., involuntary urination negatively affecting daily life.

Urinary incontinence is divided into true incontinence, stress urinary incontinence, urge incontinence, overflow incontinence, etc., and urinary incontinence is caused by functional failures of tissues or ligaments connecting the vaginal wall, the pelvic muscles and the pubic bones or weakness in the urethral sphincter, and common causes are repetitive deformation of the pelvic muscles, pregnancy and delivery, operations, loss of tension of the pelvic muscles, etc.

Due to urinary incontinence caused by the above-described various causes, when abdominal pressure is increased by laughing, coughing, sneezing, exercise, etc., urine unconsciously leaks through the urethra and, thus, a female having urinary incontinence symptoms experiences great inconvenience in her daily life.

Korean Registered Utility Model No. 20-332533 proposes a treatment instrument for urinary incontinence which treats urinary incontinence.

In Korean Registered Utility Model No. 20-332533, a mesh tape having a considerably long length is manufactured so as to penetrate the lower abdomen through a female vaginal wall and then to be exposed to the outside, and the mesh tape is implanted into the human body by a Transobturator vaginal tape (TOT) surgery which is well known in the medicine.

Both the mesh tape disclosed in Korean Registered Utility Model No. 20-332533 and a general mesh tape for TOT surgery provided to treat urinary incontinence have a structure in which both ends of the mesh tape sequentially pass through the inside of the lower abdominal tissues via a female vaginal wall and then are exposed to the outside through both incisional parts of the lower abdomen.

In order to stably fix the mesh tape to the inside of the lower abdominal tissues to support the urethra without movement or slip, in addition to the central part of the mesh tape supporting the urethra, both side parts of the mesh tape having a long length need to be implanted into the lower abdominal tissues.

However, if the mesh tape disclosed in Korean Registered Utility Model No. 20-332533 is excessively deeply inserted and fixed into the lower abdominal tissues of a female patient, the mesh tape excessively strongly presses the urethra and the female patient may have difficulty in urinating.

Further, in order to adjust the tension of the mesh tape inserted and fixed into the lower abdominal tissues of the female patient, the mesh tape should be inconveniently pulled in the outward direction of the lower abdominal tissues of the female patient and, thus, it is difficult to adjust the tension of the mesh tape.

Moreover, when sling surgery for treating urinary incontinence of a young woman is carried out, as she grows old, the tension of the mesh tape is excessively strongly applied according to a hardening process of human tissues and thus a possibility of increasing a residual urine mass may be increased.

Therefore, using biodegradable substances which are naturally absorbed by the human body as a designated time from application of a mesh tape passes, the mesh tape may maintain a high tension at the initial stage and then have a slightly lower tension after the designated time passes.

(Patent Document 1) Korean Registered Utility Model No. 20-332533

DISCLOSURE

Technical Problem

Therefore, the present invention has been made in view of the above problems, and it is an object of the present invention to provide a sling for urinary incontinence surgery which prevents a mesh tape from excessively strongly pressing the urethra and thus allows a female patient to easily urinate, and further, in order to adjust tension of the mesh tape inserted and fixed into lower abdominal tissues of the female patient, doesn't need to pull both sides of the mesh tape in the outward direction of the lower abdominal tissues of the female patient and thus facilitates tension adjustment of the mesh tape.

Technical Solution

In accordance with an aspect of the present invention, the above and other objects can be accomplished by the provision of a sling for urinary incontinence surgery comprising a mesh tape lifting, supporting and fixing a urethra when urinary incontinence surgery is performed, wherein a spacing unit is provided at the central part of the mesh tape so as to space the mesh tape and the urethra apart from each other by a designated interval during urinary incontinence surgery.

The mesh tape may be formed of carbon fiber.

The spacing unit may include a spacing member disposed at the rear of the mesh tape so as to be disposed between the mesh tape and the urethra during urinary incontinence surgery, and a fixing member configured to separably fix the spacing member to the central part of the mesh tape.

The spacing member may have a platy shape.

Otherwise, the spacing member may protrude so as to be convex in the direction of the urethra.

The spacing member may have a thickness of 2 mm~10 mm.

The spacing member may have a width of 2 mm~20 mm.

The spacing member may be formed of silicon.

The fixing member may include an extension extending forward from the upper end of the spacing member, and a latch fixing member extending downward from the end of the extension so as to surround a part or the entirety of the mesh tape.

A protrusion may be formed at the end of the latch fixing member.

The fixing member may include a wire provided with an upper end fixed to the upper part of the spacing member and a lower end fixed to the lower part of the spacing member under the condition that the wire surrounds the mesh tape.

The upper and lower ends of a plurality of wires may be fixed to the upper and lower parts of the spacing member while being spaced apart from each other by a designated interval under the condition that the wires surround the mesh tape.

The fixing member may include a wire provided with one end penetrating any one of a plurality of through holes of the mesh tape and then fixed to one side of the spacing member and the other end penetrating another one of the through holes of the mesh tape and then fixed to the other side of the spacing member.

Otherwise, the fixing member may include a main wire provided with an upper end fixed to the upper part of the spacing member and a lower end fixed to the lower part of the spacing member under the condition that the main wire surrounds the mesh tape, and a subsidiary wire provided with one end penetrating any one of a plurality of through holes of the mesh tape and then fixed to one side of the spacing member and the other end penetrating another one of the through holes of the mesh tape and then fixed to the other side of the spacing member such that the subsidiary wire intersects the main wire.

The wire may be cut by a cutting member including scissors after urinary incontinence surgery.

The spacing unit may further include a string member provided with a lower part fixed to the upper part of the spacing member.

The spacing unit may be formed of a biodegradable substance.

Advantageous Effects

In a sling for urinary incontinence surgery in accordance with the present invention, a spacing unit, which is located at the central part of a mesh tape lifting, supporting and fixing the urethra during urinary incontinence treatment surgery and is separated from the mesh tape or absorbed by the body after urinary incontinence treatment surgery, may more easily space the mesh tape and the urethra apart from each other by a designated interval, and particularly, prevent the mesh tape from excessively strongly pressing the urethra and thus allow a female patient to easily urinate, and further, in order to adjust tension of the mesh tape inserted and fixed into the lower abdominal tissues of the female patient, there is no need to pull both sides of the mesh tape in the outward direction of the lower abdominal tissues of the female patient and thus tension adjustment of the mesh tape may be facilitated.

BEST MODE

Hereinafter, preferred embodiments of the present invention will be apparently described with reference to the annexed drawings. Those skilled in the art will appreciate that various modifications, additions, and substitutions to the specific elements are possible, without departing from the scope and spirit of the invention as disclosed in the accompanying claims.

Figure 1:
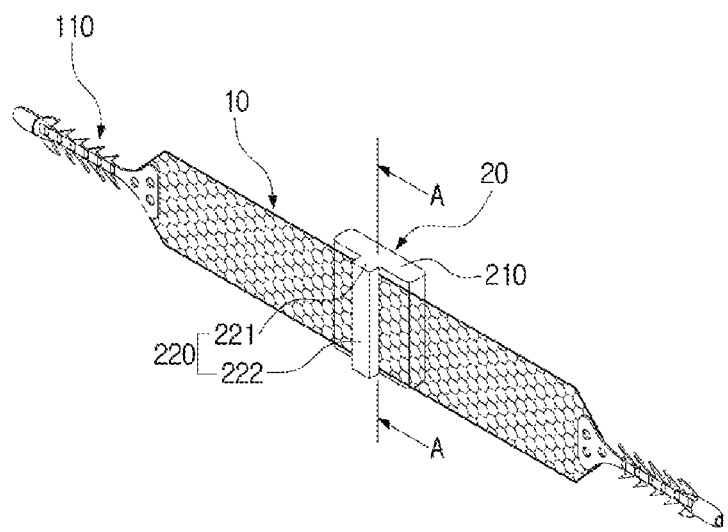
FIG. 1 is a perspective view schematically illustrating a sling for urinary incontinence surgery in accordance with a first embodiment of the present invention.
Figure 2:
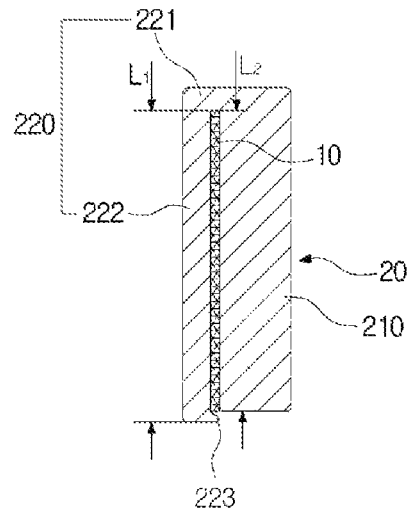
FIG. 2 is a cross-sectional view taken along line A-A of FIG. 1.

FIG. 1 is a perspective view schematically illustrating a sling for urinary incontinence surgery in accordance with a first embodiment of the present invention, and FIG. 2 is a cross-sectional view taken along line A-A of FIG. 1.

The sling for urinary incontinence surgery in accordance with a first embodiment of the present invention includes, as exemplarily shown in FIGS. 1 and 2, a mesh tape 10 which lifts, supports and fixes the urethra 3 (in FIGS. 12 and 13) when urinary incontinence surgery is performed.

The mesh tape 10 may be, as one example, although is not shown in the drawings, a mesh tape 10 configured such that both sides thereof pass through the inside of lower abdominal tissues via a female vaginal wall and are then exposed to the outside through both incisional parts of the lower abdomen, but is not limited thereto.

The mesh tape 10 may be, as another example, as exemplarily shown in FIG. 2, a mesh tape 10 provided with anchors 110 formed at one side of the mesh tape 10 and the other side of the mesh tape 10 so as to be inserted into surgical sites of a female patient and connected to skin tissues of the surgical sites, or the mesh tape 10 may be one of various kinds of mesh tapes 10.

Although the mesh tape 10 or the mesh tape 10 and the anchors 110 may be formed of various materials, they may be formed of carbon fiber.

Particularly, the mesh tape 10 or both the mesh tape 10 and the anchors 110 may be formed of carbon which is harmless to the human body, out of carbon fibers and, if the mesh tape 10 or both the mesh tape 10 and the anchors 110 are formed of carbon, the mesh tape 10 and the anchors 110 may be formed to have a small thickness, cutting of the mesh tape 10 and the anchors 110 may be prevented during a surgical process of the mesh tape 10 and the anchors 110 at a surgical site of a female patient, and elasticity of the mesh tape 10 and the anchors 110 may be improved.

A spacing unit 20 is provided at the central part of the mesh tape 10.

The spacing unit 20 is fixed to the central part of the mesh tape 10 so as to be separable by an operator, such as a surgeon, under the condition that the spacing unit 10 receives the central part of the mesh tape 10 therein.

Figure 12:
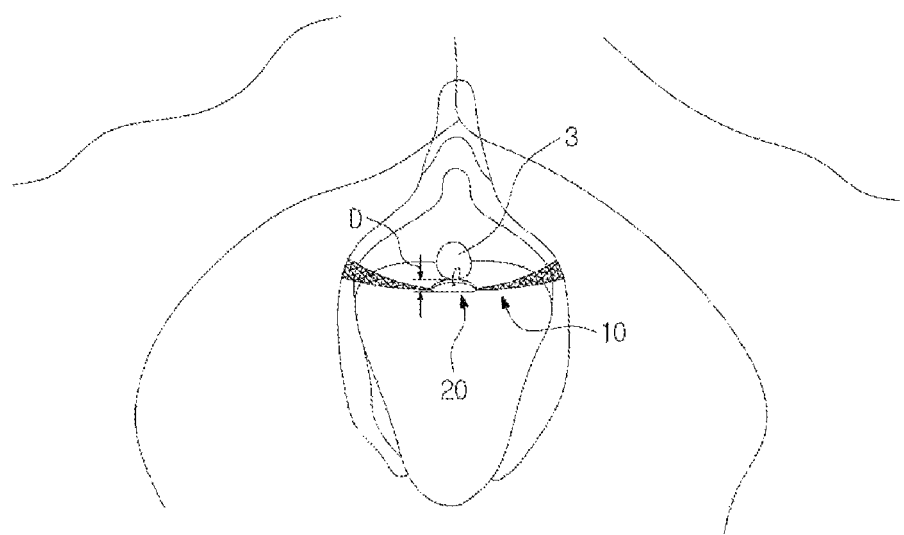
FIGS. 12 and 13 are views schematically illustrating a process of lifting, supporting and fixing the urethra by a mesh tape.

The spacing unit 20 spaces the mesh tape 10 and the urethra 3 apart from each other so that the urethra 3 is spaced apart from the lower surface of the mesh tape 10 in the upward direction of the mesh tape 10 by a designated interval D (in FIG. 12) during urinary incontinence surgery (with reference to FIG. 12).

Figure 13:
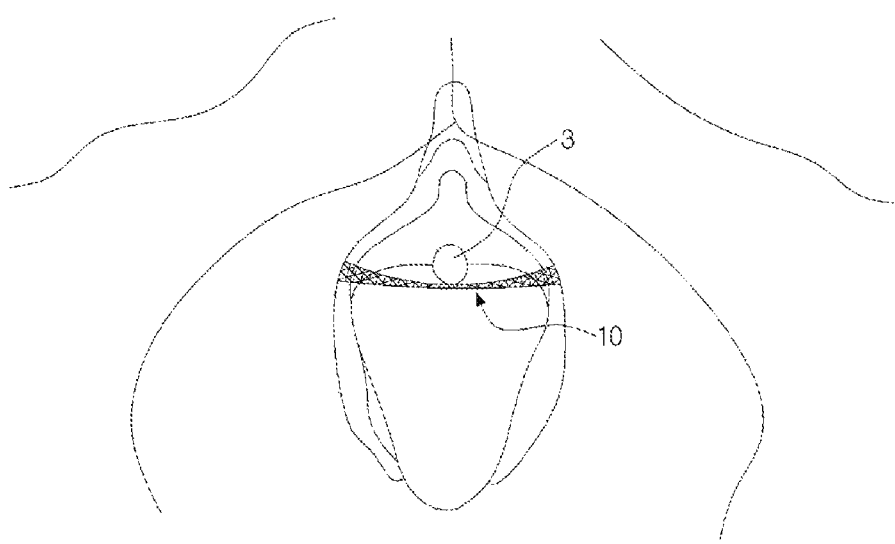

After urinary incontinence surgery, the spacing unit 20 is separated from the mesh tape 10 by an operator, such as a surgeon, and then the mesh tape 10 lifts, supports and fixes the urethra at a tension at which the female patient may easily urinate (with reference to FIG. 13).

The spacing unit 20 may include a spacing member 210 and a fixing member 220, as exemplarily shown in FIGS. 1 and 2.

The spacing member 210 having a platy shape may be vertically disposed at the rear of the mesh tape 10 so as to be disposed between the mesh tape 10 and the urethra 3.

The fixing member 220 having a bar shape may be vertically disposed at the rear of the mesh tape 10 so as to separably fix the spacing member 210 to the central part of the mesh tape 10.

In more detail, the fixing member 220 may include an extension 221 and a latch fixing member 222, as exemplarily shown in FIGS. 1 and 2.

The extension 221 may extend from the upper end of the front surface of the spacing member 210 to a designated length in the forward direction of the spacing member 210.

The latch fixing member 222 may extend vertically from the lower end of the extension 221 in the downward direction of the extension 221 so as to surround a part of the mesh tape 10 or the entirety of the mesh tape 10.

Although not shown in the drawings, as one example, in order to cause the latch fixing member 222 to surround a part of the mesh tape 10, the vertical length $L_1$ of the latch fixing member 222 may be shorter than the vertical length $L_2$ of the mesh tape 10.

Alternatively, as another example, in order to cause the latch fixing member 222 to surround the entirety of the mesh tape 10, the vertical length $L_1$ of the latch fixing member 222 may be longer than the vertical length $L_2$ of the mesh tape 10, as exemplarily shown in FIG. 2.

Further, in order to prevent the spacing unit 20 from being easily separated from the central part of the mesh tape 10, a protrusion 223 horizontally protruding in the rearward direction of the latch fixing member 222 may be formed integrally with the lower end of the rear surface of the latch fixing member 222, as exemplarily shown in FIG. 2.

If the latch fixing member 222 surrounds a part of the mesh tape 10, although not shown in the drawings, the protrusion 223 may be fixed to the mesh tape 10 under the condition that the protrusion 223 penetrates any one of a plurality of through holes 11 (in FIG. 9), which is formed on the surface of the mesh tape 10 by designated intervals.

If the latch fixing member 222 surrounds the entirety of the mesh tape 10, the protrusion 223 may fixed to the mesh tape 10 under the condition that the protrusion 223 contacts the lower part of the mesh tape 10, as exemplarily shown in FIG. 2.

Figure 3:
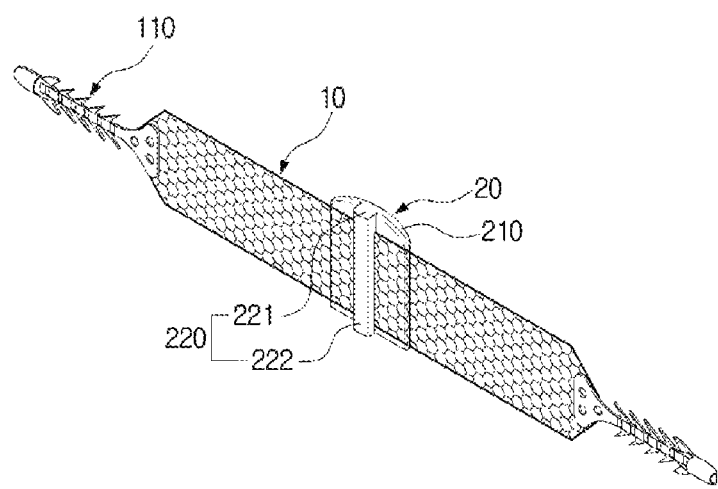
FIG. 3 is a perspective view schematically illustrating a sling for urinary incontinence surgery in accordance with a second embodiment of the present invention.
Figure 4:
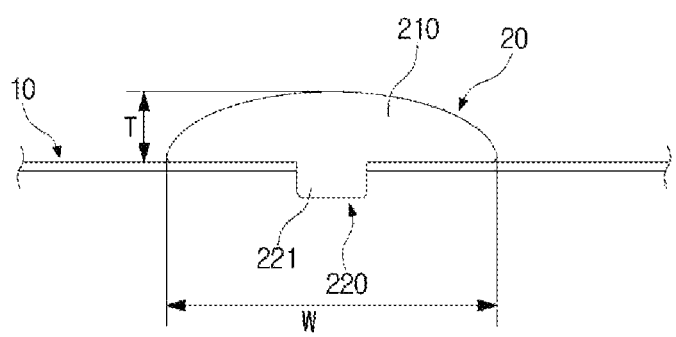
FIG. 4 is a plan view of FIG. 3.

FIG. 3 is a perspective view schematically illustrating a sling for urinary incontinence surgery in accordance with a second embodiment of the present invention, and FIG. 4 is a plan view of FIG. 3.

The sling for urinary incontinence surgery in accordance with the second embodiment of the present invention includes a mesh tape 10 and a spacing unit 20, and the rear surface of a spacing member 210 of the spacing unit 20 may protrude in an arc shape so as to be convex in the direction of the urethra 3, as exemplarily shown in FIGS. 3 and 4.

Since the rear surface of the spacing member 210 is convex in the direction of the urethra 3, the central part of the rear surface of the spacing member 210 may more easily maintain a designated interval between the central part of the mesh tape 10 and the urethra 3.

Figure 5:
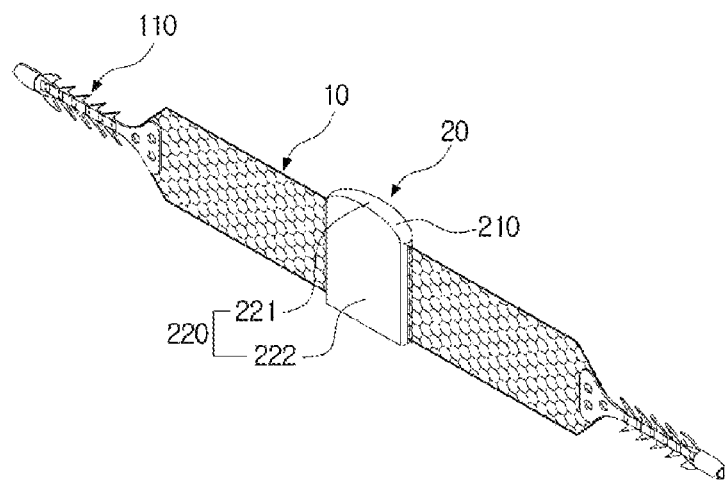
FIG. 5 is a perspective view schematically illustrating a sling for urinary incontinence surgery in accordance with a third embodiment of the present invention.

FIG. 5 is a perspective view schematically illustrating a sling for urinary incontinence surgery in accordance with a third embodiment of the present invention.

The sling for urinary incontinence surgery in accordance with the third embodiment of the present invention includes a mesh tape 10 and a spacing unit 20, and a fixing member 220 of the spacing unit 20 may extend vertically from a spacing member 210 so as to have the same lateral width as the spacing member 210, as exemplarily shown in FIG. 5.

Figure 6:
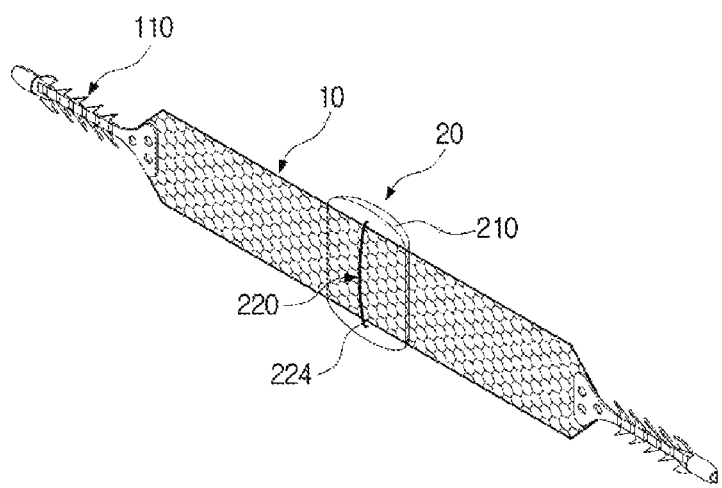
FIG. 6 is a perspective view schematically illustrating a sling for urinary incontinence surgery in accordance with a fourth embodiment of the present invention.
Figure 7:
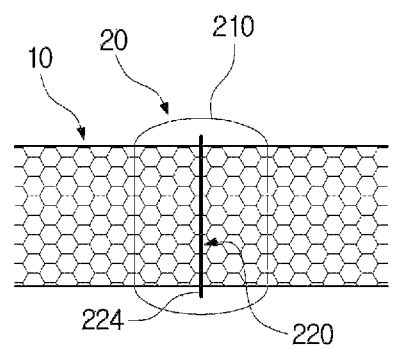
FIG. 7 is a front view of FIG. 6.

FIG. 6 is a perspective view schematically illustrating a sling for urinary incontinence surgery in accordance with a fourth embodiment of the present invention, and FIG. 7 is a front view of FIG. 6.

The sling for urinary incontinence surgery in accordance with the fourth embodiment of the present invention includes a mesh tape 10 and a spacing unit 20, and a fixing member 220 of the spacing unit 20 may include a wire 224, as exemplarily shown in FIGS. 6 and 7.

The upper end of the wire 224 may be fixed to the upper part of the front surface of a spacing member 210 through various methods, such as fixing by adhesion, etc., and the lower end of the wire 224 may be fixed to the lower part of the front surface of the spacing member 210 through various methods, such as fixing by adhesion, etc., so that the wire 224 may surround the mesh tape 10.

Figure 8:
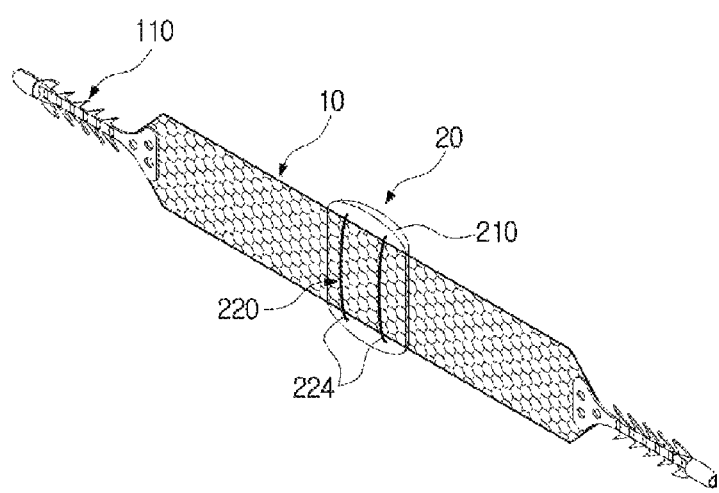
FIG. 8 is a perspective view schematically illustrating a sling for urinary incontinence surgery in accordance with a fifth embodiment of the present invention.

FIG. 8 is a perspective view schematically illustrating a sling for urinary incontinence surgery in accordance with a fifth embodiment of the present invention.

The sling for urinary incontinence surgery in accordance with the fifth embodiment of the present invention includes a mesh tape 10 and a spacing unit 20, and a fixing member 220 of the spacing unit 20 may include a plurality of wires 224, as exemplarily shown in FIG. 8.

The upper ends of the wires 224 may be fixed to the upper part of the front surface of a spacing member 210 through various methods, such as fixing by adhesion etc., while being spaced apart from each other by a designated interval, and the lower ends of the wires 224 may be fixed to the lower part of the front surface of the spacing member 210 through various methods, such as fixing by adhesion, etc., while being spaced apart from each other by a designated interval, so that the two or more wires 224 may surround the mesh tape 10.

Figure 9:
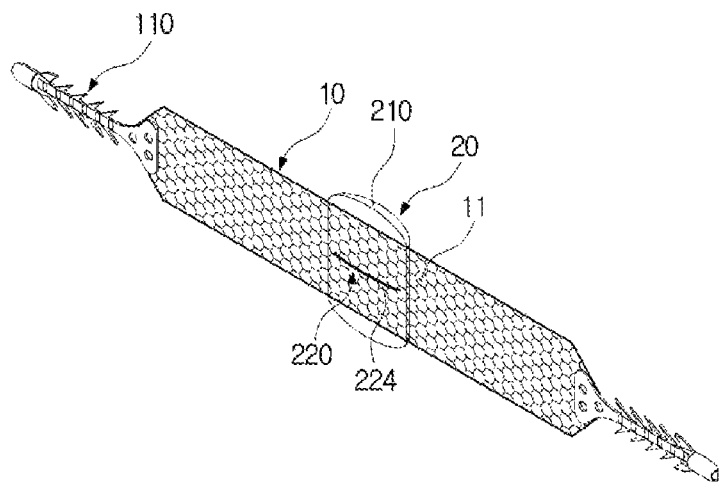
FIG. 9 is a perspective view schematically illustrating a sling for urinary incontinence surgery in accordance with a sixth embodiment of the present invention.

FIG. 9 is a perspective view schematically illustrating a sling for urinary incontinence surgery in accordance with a sixth embodiment of the present invention.

The sling for urinary incontinence surgery in accordance with the sixth embodiment of the present invention includes a mesh tape 10 and a spacing unit 20, and, in order to prevent the spacing unit 20 from moving in a direction from one side of the mesh tape 10 to the other side of the mesh tape 10, the spacing unit 20 may include a wire 224 penetrating the mesh tape 10 and fixed to a spacing member 220, as exemplarily shown in FIG. 9.

In more detail, one end of the wire 224 may penetrate any one of a plurality of through holes 11 of the mesh tape 10 located at one side of the front surface of a spacing member 210 and then be fixed to one side of the front surface of the spacing member 210 through various methods, such as fixing by adhesion, etc.

The other end of the wire 224 may penetrate another one of the through holes 11 of the mesh tape 10 located at the other side of the front surface of the spacing member 210 and then be fixed to the other side of the front surface of the spacing member 210 through various methods, such as fixing by adhesion, etc.

Figure 10:
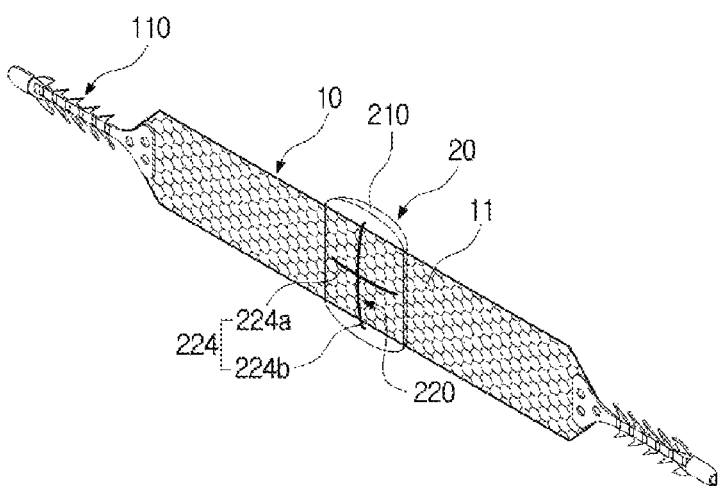
FIG. 10 is a perspective view schematically illustrating a sling for urinary incontinence surgery in accordance with a seventh embodiment of the present invention.

FIG. 10 is a perspective view schematically illustrating a sling for urinary incontinence surgery in accordance with a seventh embodiment of the present invention.

The sling for urinary incontinence surgery in accordance with the seventh embodiment of the present invention includes a mesh tape 10 and a spacing unit 20, and a fixing member 220 of the spacing unit 20 may include a main wire 224a and a subsidiary wire 224b, as exemplarily shown in FIG. 10.

The main wire 224a has the same structure as the wire 224 shown in FIGS. 6 and 7 in accordance with the fourth embodiment and the subsidiary wire 224b intersecting the main wire 224a at right angles has the same structure as the wire 224 shown in FIG. 9 in accordance with the sixth embodiment, and a detailed description thereof will thus be omitted because it is considered to be unnecessary.

The wires 224 of the above-described fixing members 220 in accordance with the fourth, fifth, sixth and seventh embodiments may be cut by a cutting member (not shown), such as scissors or a surgical knife, after urinary incontinence surgery and, thereby, an operator, such as a surgeon, may easily separate the spacing unit 20 from the mesh tape 10 after urinary incontinence surgery.

Figure 11:
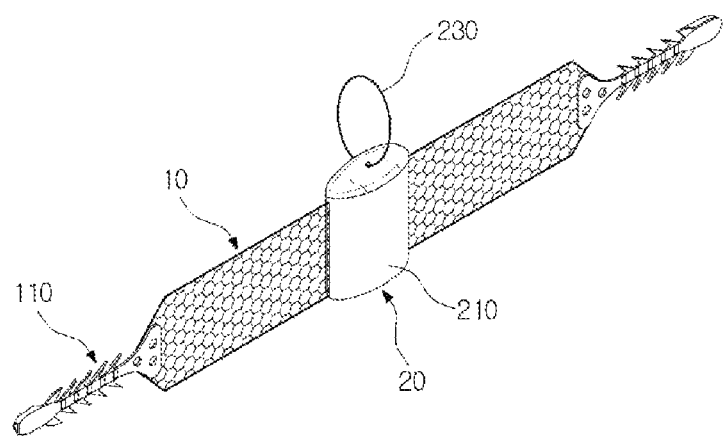
FIG. 11 is a perspective view schematically illustrating a sling for urinary incontinence surgery in accordance with an eighth embodiment of the present invention.

FIG. 11 is a perspective view schematically illustrating a sling for urinary incontinence surgery in accordance with an eighth embodiment of the present invention.

The sling for urinary incontinence surgery in accordance with the eighth embodiment of the present invention includes a mesh tape 10 and a spacing unit 20, and an upper part of the spacing unit 20 located in the upward direction of the mesh tape 10 may have a flat platy shape so that the thickness of the front part of the spacing unit 20 in the anterior-posterior direction is less than the thickness of other parts of the spacing unit 20 except for the front part of the spacing unit 20, as exemplarily shown in FIG. 11.

Further, as exemplarily shown in FIG. 11, a string member 230 including a ring-shaped wire, etc. may be provided at the upper parts of the spacing members 210 of the spacing units 20 in accordance with the first, second, third, fourth, fifth, sixth, seventh and eighth embodiments.

For example, the lower part of the string member 230 including a ring-shaped wire, etc. may penetrate the upper part of the spacing member 210 of the spacing unit 20, as exemplarily shown in FIG. 11.

After urinary incontinence surgery, an operator, such as a surgeon, may pull the string member 230 in the upward direction of the mesh tape 10, thus more easily separating the spacing unit 20 from the mesh tape 10.

In order to allow the mesh tape 10 to lift, support and fix the urethra 3 at a tension at which the female patient may easily urinate, the thicknesses T (in FIG. 4) of the spacing members 210 in accordance with the first, second, third, fourth, fifth, sixth, seventh and eighth embodiments in the anterior-posterior direction, i.e., the length from the front part of the spacing member 210 to the rear part of the spacing member 210, may be 2 mm to 10 mm.

The widths W (in FIG. 4) of the spacing members 210 in accordance with the first, second, third, fourth, fifth, sixth, seventh and eighth embodiments in the lateral direction, i.e., the length from one side of the spacing member 210 to the other side of the spacing member 210, may be 2 mm to 20 mm.

If the thickness T of the spacing member 210 in the anterior-posterior direction is less than 2 mm and the width W of the spacing member 210 in the lateral direction is less than 2 mm, the tension of the mesh tape 10 is excessively high and thus the female patient may have difficulty in urinating.

If the thickness T of the spacing member 210 in the anterior-posterior direction exceeds 10 mm and the width W of the spacing member 210 in the lateral direction exceeds 20 mm, the tension of the mesh tape 10 is excessively low so that the mesh tape 10 is loosened and may thus have difficulty in effectively lifting and supporting the urethra 3.

In order to prevent a part of the urethra contacting one of the spacing members 210 in accordance with the first, second, third, fourth, fifth, sixth, seventh and eighth embodiments, the spacing members 210 in accordance with the first, second, third, fourth, fifth, sixth, seventh and eighth embodiments may be formed of soft silicon, etc.

Otherwise, the spacing unit 20 may be formed of a biodegradable substance.

The biodegradable substance is gradually absorbed by the human body within several days to several months under the condition that the biodegradable substance contacts the urethra and may thus improve collagen regenerative capability and increase muscular strength of the urethral sphincter, and the biodegradable substance may include one selected from the group consisting of polyglycolide (PGA), polydioxanone (PDO), poly ε-caprolactone (PCL), poly lactide-co-glycolide (PLGA), poly lactide-co caprolactone (PLCL), poly-L-lactide (PLLA), polylactide (PLA) and poly β-hydroxybutyrate (PHB), which have very excellent collagen regenerative capability, or a copolymer thereof, or include one of various kinds of sponge-shaped gelatin, gelfoam, etc.

If the spacing member 210 is formed of a biodegradable substance which is absorbed by the human body within several days to several months, an operator, such as a surgeon, doesn't have to separate the spacing unit 20 from the mesh tape 10 using a cutting member (not shown), such as scissors or a surgical knife, and a patient may easily urinate after urinary incontinence surgery.

Further, the biodegradable substance, which is gradually absorbed by the human body within several days to several months under the condition that it contacts the urethra, may be easily used for the purpose of stopping bleeding, the mesh tape 10 may maintain high tension for a designated time due to the biodegradable substance gradually absorbed by the human body under the condition that it contacts the urethra and, as the designated time passes, after the biodegradable substance 30 is completely absorbed by the human body, the tension of the mesh tape 10 may be lowered such that the mesh tape 10 is slightly loosened.

FIGS. 12 and 13 are views schematically illustrating a process of lifting, supporting and fixing the urethra 3 by the mesh tape 10.

As apparent from the above description, in the sling for urinary incontinence surgery in accordance with the present invention, as exemplarily shown in FIGS. 12 and 13, the spacing unit 20, which is located at the central part of the mesh tape 10 lifting, supporting and fixing the urethra 3 during urinary incontinence treatment surgery and is separated from the mesh tape 10 or absorbed by the body after urinary incontinence treatment surgery, may more easily space the mesh tape 10 and the urethra 3 apart from each other by a designated interval, and particularly, prevent the mesh tape 10 from excessively strongly pressing the urethra 3 and thus allow a female patient to easily urinate, and further, in order to adjust tension of the mesh tape 10 inserted and fixed into the lower abdominal tissues of the female patient, there is no need to pull both sides of the mesh tape 10 in the outward direction of the lower abdominal tissues of the female patient and thus tension adjustment of the mesh tape 10 may be facilitated.

The invention claimed is:

1. A sling for urinary incontinence surgery, the sling comprising a mesh tape for lifting, supporting and fixing a urethra when urinary incontinence surgery is performed,
wherein a spacing unit, provided at a central part of the mesh tape and spacing the mesh tape and the urethra apart from each other by a designated interval during urinary incontinence surgery, includes:
a spacing member disposed at a rear of the mesh tape so as to be disposed between the mesh tape and the urethra during urinary incontinence surgery and having a thickness in an anterior-posterior direction of 2 mm~10 mm and a width in a lateral direction of 2 mm~20 mm;
a fixing member configured to separably fix the spacing member to the central part of the mesh tape and including an extension extending forward from an upper end of the spacing member and a latch fixing member extending downward from a lower end of the extension so as to surround the mesh tape and provided with a protrusion formed at a lower end of a rear surface thereof; and
a string member provided with a lower part fixed to an upper part of the spacing member.

2. A sling for urinary incontinence surgery, the sling comprising a mesh tape for lifting, supporting and fixing a urethra when urinary incontinence surgery is performed,
wherein a spacing unit, provided at a central part of the mesh tape and spacing the mesh tape and the urethra apart from each other by a designated interval during urinary incontinence surgery, includes:
a spacing member disposed at a rear of the mesh tape so as to be disposed between the mesh tape and the urethra during urinary incontinence surgery and having a thickness in an anterior-posterior direction of 2 mm~10 mm and a width in a lateral direction of 2 mm~20 mm;
a fixing member including a wire provided with upper and lower ends respectively fixed to upper and lower parts of the spacing member under a condition that the wire surrounds the mesh tape; and
a string member provided with a lower part fixed to the upper part of the spacing member.

3. A sling for urinary incontinence surgery, the sling comprising a mesh tape for lifting, supporting and fixing a urethra when urinary incontinence surgery is performed,
wherein a spacing unit, provided at a central part of the mesh tape and spacing the mesh tape and the urethra apart from each other by a designated interval during urinary incontinence surgery, includes:
a spacing member disposed at a rear of the mesh tape so as to be disposed between the mesh tape and the urethra during urinary incontinence surgery and having a thickness in an anterior-posterior direction of 2 mm~10 mm and a width in a lateral direction of 2 mm~20 mm;
a fixing member including a plurality of wires provided with upper end lower ends respectively fixed to upper and lower parts of the spacing member while being spaced apart from each other by a designated interval under a condition that the wires surround the mesh tape; and
a string member provided with a lower part fixed to the upper part of the spacing member.

4. A sling for urinary incontinence surgery, the sling comprising a mesh tape for lifting, supporting and fixing a urethra when urinary incontinence surgery is performed,
wherein a spacing unit, provided at a central part of the mesh tape and spacing the mesh tape and the urethra apart from each other by a designated interval during urinary incontinence surgery, includes:
a spacing member disposed at a rear of the mesh tape so as to be disposed between the mesh tape and the urethra during urinary incontinence surgery and having a thickness in an anterior-posterior direction of 2 mm~10 mm and a width in a lateral direction of 2 mm~20 mm;
a fixing member including a wire provided with one end penetrating any one of a plurality of through holes of the mesh tape and then fixed to one side of the spacing member and another end penetrating another one of the through holes of the mesh tape and then fixed to another side of the spacing member; and
a string member provided with a lower part fixed to an upper part of the spacing member.

5. A sling for urinary incontinence surgery, the sling comprising a mesh tape for lifting, supporting and fixing a urethra when urinary incontinence surgery is performed,
wherein a spacing unit, provided at a central part of the mesh tape and spacing the mesh tape and the urethra apart from each other by a designated interval during urinary incontinence surgery, includes:
a spacing member disposed at a rear of the mesh tape so as to be disposed between the mesh tape and the urethra during urinary incontinence surgery and having a thickness in an anterior-posterior direction of 2 mm~10 mm and a width in a lateral direction of 2 mm~20 mm;
a fixing member including a main wire provided with an upper end fixed to an upper part of the spacing member and a lower end fixed to a lower part of the spacing member under a condition that the main wire surrounds the mesh tape, and a subsidiary wire provided with one end penetrating any one of a plurality of through holes of the mesh tape and then fixed to one side of the spacing member and another end penetrating another one of the through holes of the mesh tape and then fixed to another side of the spacing member such that the subsidiary wire intersects the main wire; and
a string member provided with a lower part fixed to the upper part of the spacing member.

6. The sling for urinary incontinence surgery according to claim 1, wherein, in order to cause the latch fixing member to surround a part of the mesh tape, a vertical length of the latch fixing member is shorter than a vertical length of the mesh tape, and the protrusion penetrates any one of a plurality of through holes of the mesh tape and is then fixed to the mesh tape.

7. The sling for urinary incontinence surgery according to claim 1, wherein the mesh tape is formed of carbon fiber.

8. The sling for urinary incontinence surgery according to claim 1, wherein the spacing member has a platy shape.

9. The sling for urinary incontinence surgery according to claim 1, wherein the spacing member protrudes so as to be convex in a direction of the urethra.

10. The sling for urinary incontinence surgery according to claim 1, wherein the spacing member is formed of silicon.

11. The sling for urinary incontinence surgery according to claim 2, wherein the wire is cut by a cutting member including scissors after urinary incontinence surgery.

12. The sling for urinary incontinence surgery according to claim 1, wherein the spacing unit is formed of a biodegradable substance.

13. The sling for urinary incontinence surgery according to claim 2, wherein the mesh tape is formed of carbon fiber.

14. The sling for urinary incontinence surgery according to claim 3, wherein the mesh tape is formed of carbon fiber.

15. The sling for urinary incontinence surgery according to claim 4, wherein the mesh tape is formed of carbon fiber.

16. The sling for urinary incontinence surgery according to claim 5, wherein the mesh tape is formed of carbon fiber.

17. The sling for urinary incontinence surgery according to claim 6, wherein the mesh tape is formed of carbon fiber.

18. The sling for urinary incontinence surgery according to claim 2, wherein the spacing member has a platy shape.

19. The sling for urinary incontinence surgery according to claim 3, wherein the spacing member has a platy shape.

20. The sling for urinary incontinence surgery according to claim 4, wherein the spacing member has a platy shape.

21. The sling for urinary incontinence surgery according to claim 5, wherein the spacing member has a platy shape.

22. The sling for urinary incontinence surgery according to claim 6, wherein the spacing member has a platy shape.

23. The sling for urinary incontinence surgery according to of claim 2, wherein the spacing member protrudes so as to be convex in a direction of the urethra.

24. The sling for urinary incontinence surgery according to of claim 3, wherein the spacing member protrudes so as to be convex in a direction of the urethra.

25. The sling for urinary incontinence surgery according to of claim 4, wherein the spacing member protrudes so as to be convex in a direction of the urethra.

26. The sling for urinary incontinence surgery according to of claim 5, wherein the spacing member protrudes so as to be convex in a direction of the urethra.

27. The sling for urinary incontinence surgery according to of claim 6, wherein the spacing member protrudes so as to be convex in a direction of the urethra.

28. The sling for urinary incontinence surgery according to of claim 2, wherein the spacing member is formed of silicon.

29. The sling for urinary incontinence surgery according to of claim 3, wherein the spacing member is formed of silicon.

30. The sling for urinary incontinence surgery according to of claim 4, wherein the spacing member is formed of silicon.

31. The sling for urinary incontinence surgery according to of claim 5, wherein the spacing member is formed of silicon.

32. The sling for urinary incontinence surgery according to of claim 6, wherein the spacing member is formed of silicon.

33. The sling for urinary incontinence surgery according to claim 3, wherein the wire is cut by a cutting member including scissors after urinary incontinence surgery.

34. The sling for urinary incontinence surgery according to claim 4, wherein the wire is cut by a cutting member including scissors after urinary incontinence surgery.

35. The sling for urinary incontinence surgery according to claim 5, wherein the wire is cut by a cutting member including scissors after urinary incontinence surgery.

36. The sling for urinary incontinence surgery according to claim 2, wherein the spacing unit is formed of a biodegradable substance.

37. The sling for urinary incontinence surgery according to claim 3, wherein the spacing unit is formed of a biodegradable substance.

38. The sling for urinary incontinence surgery according to claim 4, wherein the spacing unit is formed of a biodegradable substance.

39. The sling for urinary incontinence surgery according to claim 5, wherein the spacing unit is formed of a biodegradable substance.

40. The sling for urinary incontinence surgery according to claim 6, wherein the spacing unit is formed of a biodegradable substance.

* * * * *